United States Patent
Frautschi (12)

(10) Patent No.: US 6,210,437 B1
(45) Date of Patent: Apr. 3, 2001

(54) CHEMICAL METHOD TO BOND SILICONE TO METAL

(75) Inventor: Jack R. Frautschi, Athens, TX (US)

(73) Assignee: Sulzer Orthopedics Inc., Austin, TX (US)

( * ) Notice: Subject to any disclaimer, the term of this patent is extended or adjusted under 35 U.S.C. 154(b) by 0 days.

(21) Appl. No.: 09/148,014

(22) Filed: Sep. 4, 1998

(51) Int. Cl.⁷ .............................. A61F 2/24; A61F 2/06; A61L 27/16
(52) U.S. Cl. ............ 623/1.46; 427/2.24; 427/2.25; 427/2.26; 623/900; 623/901
(58) Field of Search .................... 623/1, 11, 12, 623/901, 1.46, 900; 427/2.24, 2.25, 2.26

(56) References Cited

U.S. PATENT DOCUMENTS

| | | | |
|---|---|---|---|
| 4,652,459 | * 3/1987 | Englehaardt | 623/16 |
| 5,356,433 | * 10/1994 | Rowland et al. | 623/11 |
| 5,411,553 | * 5/1995 | Gerace et al. | 623/6 |
| 5,736,251 | * 4/1998 | Pinchuk | 623/1 |

OTHER PUBLICATIONS

Hirayama et al. "Strongly Attached Untrathin polymer layers on metal surfaces obtained by activation of Si–H bonds", Appl. Surf. Sci. 143(1–4), 256–264, 1999.*

* cited by examiner

*Primary Examiner*—David H. Willse
*Assistant Examiner*—Choon P. Koh
(74) *Attorney, Agent, or Firm*—Philip S. Lyren

(57) ABSTRACT

Herein are disclosed devices, particularly medical devices, more particularly implantable medical devices, comprising a first layer of a metal and a short chain silicone terminating with silicon hydride, and a second layer of a silicone polymer. The short chain silicone is bound to the metal, and the silicone polymer is covalently bound via the vinyl group to the silicon hydride group of the short chain silicone. Also disclosed herein is a method for making such devices, involving providing the metal, depositing the short chain silicone, molding the silicone polymer as a silicone prepolymer, and polymerizing the silicone prepolymer to yield silicone polymer covalently bonded to the short chain silicone.

10 Claims, No Drawings

CHEMICAL METHOD TO BOND SILICONE TO METAL

BACKGROUND OF THE INVENTION

1. Field of the Invention

The present invention relates generally to the field of polymer coated, implantable medical devices. More particularly, it concerns such medical devices comprising a first layer of a metal bonded to a short chain silicone terminating with silicon hydride, and a second layer of a silicone polymer covalently bonded to the silicon hydride.

2. Description of Related Art

It has become common to treat a variety of medical conditions by implanting medical devices into the esophagus, trachea, colon, biliary tract, urinary tract, vascular system, or other location in the body of a human or animal patient. For example, in the vascular system, valves in the heart may weaken as a result of age, injury, or disease, impairing proper blood flow and posing a health risk to the patient. Such weakened naturally-occurring heart valves may be replaced with prosthetic heart valves.

Well-known in the art are prosthetic heart valves which comprise a polymer stent to give the valve shape, structure, and rigidity, over which is sewn tissue taken from an animal heart valve. Such prosthetic heart valves have a number of shortcomings. First, the introduction of animal tissue into another species raises the risk of adverse body responses, such as rapid thrombogenic reaction and inflammatory tissue reactions. Second, the animal tissue is mechanically connected to the stent, and thus the heart valve has low shear resistance.

Attempts have been made to construct heart valves from different materials and adhere their components in different ways. For example, metal stents have been used and animal tissue sewn over them. In another example, polymers have been used in place of animal tissue over metal stents. Polymeric materials avoid the risk of immunogenicity posed by use of animal tissue, but heart valves comprising polymeric materials covering metal stents still suffer from low shear resistance.

In order to increase the shear resistance of heart valves comprising polymeric materials covering metal stents, coupling agents, such as are available from Dow Corning, may be used. Such coupling agents aid physical adhesion of the polymeric coating to the stent, but the coated articles still have relatively low shear resistance and longevity.

Although the above discussion has focused on the example of prosthetic heart valves, it is applicable to other implantable medical devices, such as catheters, cannulae, vascular grafts, pacemaker leads, defibrillator leads, needles, and orthopedic devices, among others.

Therefore, it is desirable to have implantable medical devices which do not stimulate adverse body reactions. It is also desirable to have implantable medical devices highly resistant to forces acting to shear two components apart. It is also desirable to provide a method for making implantable devices which exhibit both of the desirable traits given above.

SUMMARY OF THE INVENTION

Herein are disclosed implantable medical devices comprising a first layer of a metal bonded to a short chain silicone terminating with a silicon hydride, and over the first layer a second layer of silicone polymer covalently bonded to the silicon hydride of the short chain silicone. The second layer of silicone polymer is non-immunogenic and renders the implantable medical device non-toxic. The chemical crosslinking of the silicone polymer to the metal via bonding to the short chain silicone gives the implantable medical device greater shear resistance than does mechanical adhesion.

In another embodiment, the present invention relates to a method for making a device, said device comprising a first layer comprising a metal and a short chain silicone terminating with silicon hydride, and a second layer comprising silicone polymer bonded to the silicon hydride of the short chain silicone. The method comprises providing the metal; depositing the short chain silicone on the outer surface of the metal under conditions in which bonding between the short chain silicone and the metal occurs, thereby forming the first layer; molding a silicone prepolymer to the outer surface of the first layer, the silicone prepolymer thereby forming a second layer; and polymerizing the silicone prepolymer to form a second layer of silicone polymer, the second layer covalently bonded to the silicon hydride of the short chain silicone in the first layer.

DESCRIPTION OF ILLUSTRATIVE EMBODIMENTS

The present invention relates to devices, particularly medical devices, more particularly medical devices for implantation, comprising a first layer of a metal and short chain silicone terminating with silicon hydride, and a second layer of a silicone polymer covalently bonded to the silicon hydride. The second layer is the outer layer of the medical device, which is adapted to come into contact with physiological fluids and/or tissue. The second layer of silicone polymer is biologically inert and non-immunogenic, and serves to protect both the metal in the first layer from attack by the body environment, and the body from high levels of metal contact or metal bleaching.

A medical device is any object fabricated for use in medicine. Implantable medical devices are those whose medical use is as a prosthesis in the body of an animal, particularly a human. An implantable medical device in accordance with the present invention can be any known in the art. A preferred implantable medical device is a heart valve. The stent of the heart valve is the first layer of metal and silicon hydride, and the outer layer of the heart valve is the second layer of silicone polymer. Other implantable medical devices that can be made in accordance to the present invention will be apparent to the skilled artisan, e.g. catheters, cannulae, vascular grafts, pacemaker leads, defibrillator leads, needles, and orthopedic devices, among other implantable medical devices with tissue-contacting surfaces.

The physical dimensions of the first layer can be any appropriate dimension to provide the size and shape of the implantable medical device, and to provide rigidity and strength. In light of the present disclosure, such physical dimensions will be apparent to one skilled in the art. The external perimeter of the device before application of the second layer is herein defined as the "subsurface" of the device. The first layer can cover another material, can be hollow, or can be solid, provided the first layer provides substantially all of the subsurface of the device.

If the first layer is applied over another material, it can be of any thickness sufficient to both provide the size, shape, rigidity, and strength described above. In this embodiment, the material over which the first layer is applied can be any material to which the metal of the first layer can bond and which has physical characteristics compatible with the intended use of the device. Exemplary materials include metals such as titanium or stainless steel, or polymers such as polyolefins (e.g. polyethylene, polypropylene, polyisobutylene, and ethylene-alphaolefin copolymers), silicone polymers (e.g. polydimethylsiloxane), acrylic polymers and copolymers (e.g. polyacrylate, polymethylmethacrylate, and polyethylacrylate), vinyl halide polymers and copolymers (e.g. polyvinyl chloride), fluoropolymers (e.g. polytetrafluoroethylene, chlorotrifluoroethylene, and fluorinated ethylenepropylene), polyvinyl ethers (e.g. polyvinyl methyl ether), polyvinylidene halides (e.g. polyvinylidene fluoride and polyvinylidene chloride), polyacrylonitrile, polyvinyl ketones, polyvinyl aromatics, polyvinyl esters, natural and synthetic rubbers, polyamides (e.g. nylon 6,6 and polycaprolactam), polyesters, and polyurethanes, among others known to one skilled in the art. Preferred materials are silicone rubbers, polyurethanes, polyesters, fluoropolymers, and polyolefins.

The metal for use in the first layer of the medical device can be any metal known for use in medical devices and capable of forming bonds with short chain silicone. Preferably, the metal is titanium, tantalum, silver, gold, vanadium, niobium, stainless steel, cobalt, chromium, or alloys thereof. More preferably, the metal is a biocompatible metal, such as titanium, tantalum, niobium, vanadium, stainless steel, silver, or gold.

A short chain silicone terminating with silicon hydride is bonded to the metal. The short chain silicone is bonded to the metal via a silicon hydroxide group that is not at the silicon-hydride terminus. In one embodiment, the short chain silicone has the formula

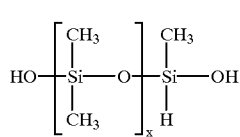

(Formula I)

wherein x is from 1 to 10. Preferably x is from 3 to 6, and more preferably x is 4.

In a second embodiment, the short chain silicone can be partially cyclical, provided that the silicon hydride group and a silicon hydroxide group provide the activities desirable in the present invention and that will be described below.

The silicone polymer in the second layer can comprise any silicone prepolymer that has both the ability to polymerize with itself and a vinyl (CH=CH$_2$) group. An exemplary silicone prepolymer has the formula

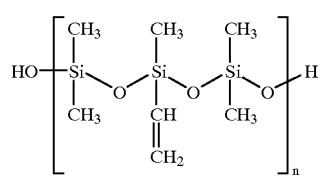

(Formula II)

wherein n is any integer greater than zero. Preferably, n is greater than or equal to 5; more preferably, n is greater than or equal to 10.

The silicone polymer is bonded to the short chain silicone via a linkage between the vinyl group of the polymer and the silicon hydride group of the short chain silicone. This covalent bond between the silicone polymer and the short chain silicone, in combination with the bond between the short chain silicone and the metal, forms a chemical linkage of the second layer to the first. An exemplary structural formula showing the linkage between a metal and a short chain silicone, and between the short chain silicone and a silicone polymer, is as follows:

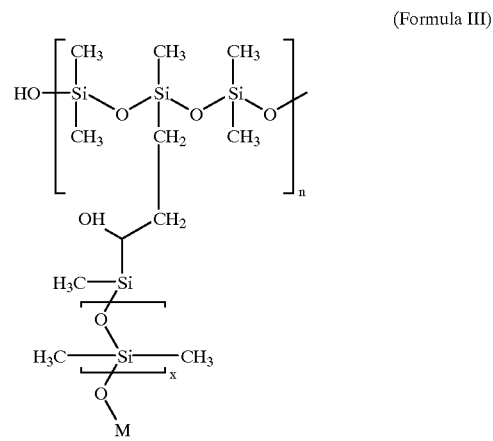

(Formula III)

wherein M is a biocompatible metal such as titanium, tantalum, niobium, vanadium, stainless steel, silver, or gold; x is an integer from 1 to 10, preferably 3 to 6, more preferably 4; and n is any integer greater than zero. In Formula III, the short chain silicone is present in the radical form:

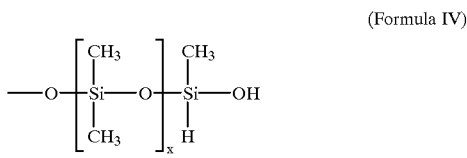

(Formula IV)

and the silicone polymer is present in the form:

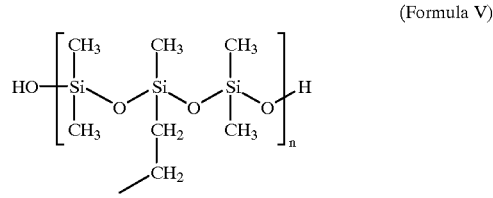

(Formula V)

The second layer can be of any thickness. It is desirable for the thickness to be great enough to ensure both the metal of the first layer is protected from the body environment and the body environment is protected from the metal of the first layer.

The present invention is also directed to a method of making devices, preferably medical devices, more preferably implantable medical devices, comprising a first layer comprising a metal and a short chain silicone terminating with silicon hydride bonded to the metal, and a second layer comprising silicone polymer bonded to the silicon hydride. The method comprises providing the metal; depositing the short chain silicone terminating with silicon hydride on the outer surface of the metal under conditions in which bonding between the short chain silicone and the metal occurs, thereby forming the first layer; molding a silicone prepolymer to the outer surface of the first layer, the silicone prepolymer thereby forming a second layer; and polymerizing the silicone prepolymer to convert the second layer into silicone polymer, the silicone polymer of the second layer covalently bonded to the silicon hydride in the first layer.

The metal is provided in a form appropriate for its use in a particular device. The metal can be formed in the shape of the device, e.g. a heart valve stent, by any appropriate technique known in the art, such as molding, machining, etc. If the metal is present as a first layer covering another material, it can be formed thereover by any appropriate technique known in the art, such as vacuum deposition, sputter deposition, or ion plating, among others.

Depositing the short chain silicone comprising a silicon hydride onto the metal can be accomplished by any method that leads to bonding of the short chain silicone to the metal. Preferably, the deposition is performed by vapor deposition or RF-plasma deposition. More preferably, the deposition is performed by RF-plasma deposition. Briefly, RF-plasma deposition involves ionization of the short chain silicone by application of electromagnetic radiation, and subsequent deposition of the ionized short chain silicone onto the metal and formation of a bond. Detailed techniques of RF-plasma deposition are known to the skilled artisan. It is desirable that the concentration of short chain silicone on the metal be high enough to bring about a density of crosslinks between the silicone polymer and the metal sufficiently high to ensure favorable physical properties of the device.

Molding the silicone prepolymer herein refers to any technique known in the art of emplacing the second layer onto the first. A preferred technique is injection molding. Briefly, injection molding involves placing the silicone prepolymer in the injection molding machine. The injection molding machine mixes and places a layer of silicone over the stent (which had been previously laden of short chain silicone). The bonding is a point catalyzed heat generated reaction. Detailed techniques of injection molding are known to the skilled artisan. It is desirable that the thickness of silicone prepolymer be at least great enough to fully coat the first layer and protect the metal from the body environment and the body environment from the metal.

Polymerizing the silicone prepolymer to yield the silicone polymer covalently bonded to the silicone hydride can be accomplished by techniques known to the art. Polymerization is aided by the application of catalyst and heat. Preferred catalysts include metals such as platinum. More preferably, the catalyst is platinum. The temperature can be any above room temperature; the preferred temperature is in the range of 120° C. to 150° C., and more preferably the temperature is in the range of 140° C.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

A heart valve is made according to the method described above. First, a titanium stent is provided of appropriate size and shape. The titanium stent is then placed in an RF-plasma deposition vessel. The short chain silicone terminating with silicon hydride is introduced in the gaseous phase into the vessel and the vessel is activated to ionize the short chain silicone. The ionized short chain silicone is then deposited on the outer surface of the stent and bonds form between the short chain silicone and the titanium via the ionized hydroxyl group. The plasma deposition continues until it has been calculated that a desired concentration of short chain silicone is bound to the titanium.

After the plasma deposition is complete, the titanium stent with deposited short chain silicone is removed from the vessel and placed in a silicone injection molding device. Silicone prepolymer is then injection molded over the titanium stent. Injection molding continues until is has been calculated that a desired thickness of the second layer has been reached.

Polymerization of the silicone prepolymer is then affected by contacting the heart valve with platinum powder catalyst at a temperature of 140° C. for four hours. The silicone prepolymer will polymerize with itself, and will also bond to the silicon hydride groups of the short chain silicone between the silicon hydrides and the vinyl groups of the silicone prepolymer.

The resulting heart valve comprises a titanium stent and an outer layer of a silicone polymer. The crosslinking of the titanium and the silicone polymer via the short chain silicone imparts greater adhesion of the outer layer to the stent than can be affected by a mechanical interface between the titanium and the silicone polymer.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An implantable medical device made according to the following process:

providing a first layer comprising a metal and a short chain silicone terminating with a silicon hydride group;

providing a silicone polymer having a vinyl group; and covalently bonding said vinyl group of said silicone polymer to said silicone hydride group of said short chain silicone to provide a second layer.

2. The device of claim 1 wherein the implantable medical device is a stent for a heart valve.

3. The device of claim 1 wherein said metal is selected from the group consisting of: titanium, tantalum, silver, gold, stainless steel, cobalt, chromium, and alloys thereof.

4. The device of claim 1 wherein the short chain silicone has the formula

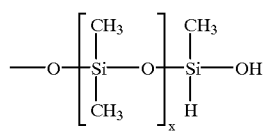

wherein x is from 1 to 10, and the short chain silicone is bonded to said metal by said —O group.

5. The device of claim 4 wherein x is 3 to 6.
6. The device of claim 4 wherein x is 4.
7. The device of claim 1 wherein said silicone polymer has the formula

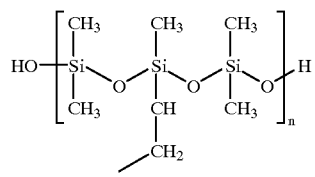

wherein n is any integer greater than zero, and said step of covalently bonding comprises covalently bonding said —CH$_2$ group to said short chain silicone.

8. The device of claim 7 wherein n is greater than or equal to 5.

9. The device of claim 7 wherein n is greater than or equal to 10.

10. An implantable medical device of the formula:

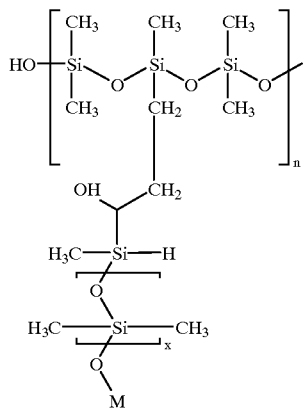

wherein M is a biocompatible metal selected from the group consisting titanium, tantalum, silver, gold, stainless steel, cobalt, chromium, and alloys thereof, x is an integer from 1 to 10, and n is any integer greater than 0.

* * * * *